(12) United States Patent
Deuel et al.

(10) Patent No.: US 10,039,470 B2
(45) Date of Patent: Aug. 7, 2018

(54) ENCEPHALOPHONE

(71) Applicants: Thomas Andrew Deuel, Seattle, WA (US); Felix Darvas, Seattle, WA (US)

(72) Inventors: Thomas Andrew Deuel, Seattle, WA (US); Felix Darvas, Seattle, WA (US)

(73) Assignee: Thomas Andrew Deuel, Seattle, WA (US)

( * ) Notice: Subject to any disclaimer, the term of this patent is extended or adjusted under 35 U.S.C. 154(b) by 0 days.

(21) Appl. No.: 14/684,538

(22) Filed: Apr. 13, 2015

(65) Prior Publication Data

US 2016/0027423 A1 Jan. 28, 2016

Related U.S. Application Data

(60) Provisional application No. 61/978,727, filed on Apr. 11, 2014.

(51) Int. Cl.
| | |
|---|---|
| *G10H 1/06* | (2006.01) |
| *A61B 5/0476* | (2006.01) |
| *G10H 1/00* | (2006.01) |
| *A61B 5/048* | (2006.01) |

(52) U.S. Cl.
CPC ......... *A61B 5/0476* (2013.01); *G10H 1/0025* (2013.01); *A61B 5/048* (2013.01); *G10H 2210/115* (2013.01); *G10H 2220/376* (2013.01)

(58) Field of Classification Search
USPC .......................................................... 84/622
See application file for complete search history.

(56) References Cited

U.S. PATENT DOCUMENTS

| | | | | |
|---|---|---|---|---|
| 3,753,433 A | * | 8/1973 | Bakerich .............. | A61B 5/0404 600/28 |
| 4,883,067 A | * | 11/1989 | Knispel ................ | A61B 5/0482 600/28 |
| 9,436,279 B2 | * | 9/2016 | Beaty ...................... | G06F 3/015 |
| 2014/0031712 A1 | * | 1/2014 | Herskovitz ............ | A61B 5/048 600/545 |

* cited by examiner

*Primary Examiner* — Christopher Uhlir
(74) *Attorney, Agent, or Firm* — Foster Pepper PLLC (57) ABSTRACT

A novel musical instrument was created using electroencephalogram (EEG) motor imagery to control a synthesized piano, and is herein named the Encephalophone. Alpha-frequency (8-12 Hz) signal power, originating from either posterior dominant rhythm (PDR) in the occipital cortex or from mu rhythm in the motor cortex, was used to create a power scale which was then converted into a musical scale which could be manipulated by the individual. Subjects could then generate different notes of the scale by activation (event-related synchronization) or de-activation (event-related desynchronization) of the PDR or mu rhythms in occipital or motor cortex, respectively.

4 Claims, 11 Drawing Sheets

ENCEPHALOPHONE

PRIORITY CLAIM

This patent application claims the benefit of U.S. Provisional Patent Application No. 61/978,727 filed Apr. 11, 2014, which is hereby incorporated by reference in its entirety.

BACKGROUND OF THE INVENTION

Since early in the history of the use of electroencephalogram (EEG) for measurement of electrical patterns of the human brain, efforts have been made to transform EEG electrical activity into sound and music. These efforts not only created alternatives to purely visual feedback, but also opened up new possibilities for artistic and musical expression, and created possible therapeutic avenues for patients with various causes of motor disability.

The earliest example of such EEG to sound conversion appears to occur in the literature shortly after the invention of the EEG. In 1934, Adrian and Matthews, replicating the earliest EEG descriptions of the posterior dominant rhythm ('the Berger rhythm') by Hans Berger in 1929, monitored their own EEG with sound.

In 1965, the composer and experimental musician Alvin Lucier created a performance involving control of percussion instruments via strength of EEG posterior dominant rhythm (PDR) at the Rose Art Museum at Brandeis University, with the encouragement and participation of composer John Cage. The performer increased and decreased the volume of percussion instruments by modulation of the PDR with opening and closing their eyes. However, they experienced some difficulty in achieving good control, and to overcome this employed a second performer manually adjusting the gain from the EEG output.

Following in Lucier's pathway 5 years later, David Rosenboom in 1970 created a performance piece called "Ecology of the Skin" for Automation House in New York, N.Y. This involved using EEG signal from ten participants processed through individualized electronic circuits to generate visual and auditory performance. More recently, in 2006, Brouse et al., created EEG waveform spectral analysis in multiple frequency bands to passively control sound and music, in a project for the eNTERFACE summer workshop.

Eduardo Miranda at the Interdisciplinary Centre for Computer Music Research (ICCMR) at Plymouth University, UK was part of that summer workshop project, and has gone on to contribute significantly to this field. In 2008, he used the changing patterns of alpha and beta frequency rhythms in EEG to act as a switch between different musical styles, and later used subject visual gaze direction to allow visual evoked potentials of EEG to control various musical parameters. More recently, Miranda and colleagues used a statistical analysis of subjective emotions and EEG in an attempt to create an emotion sensor to subconsciously allow users to select music which they associate with more subjectively positive emotions.

Mirko Pham and others used slow cortical potentials of EEG to drive control of either ascending or descending pre-set pitch sequences; they used both auditory feedback and visual feedback. While they used tone sequences for feedback, the feedback did not represent a musical context. Using this protocol, they observed significantly better results for visual than auditory feedback.

Brain Computer Interface (BCI) research has advanced significantly to allow the development of Brian Computer Music Interface (BCMI) devices. BCMI devices are simply the application of BCI technology to generate music as an output and/or feedback to the user. The creation of consciously controlled real-time EEG generation of scalar music by a user with experimentally proven accuracy has not yet been described, to the best of our knowledge.

In this paper, we describe the creation of the Encephalophone, a BCMI device that uses visual cortex posterior dominant rhythm (PDR) or motor cortex mu rhythm (mu) to consciously and volitionally control the generation of scalar music. This represents a novel musical instrument that does not require physical movement, as well as a potential therapeutic device for patients suffering from various motor deficits (e.g. amyotrophic lateral sclerosis, brainstem stroke, traumatic amputation). We additionally describe experiments demonstrating the user-controlled accuracy of the instrument by conscious cognitive processes.

BRIEF DESCRIPTION OF THE DRAWING

Preferred and alternative examples of the present invention are described in detail below with reference to the following drawing figures.

DETAILED DESCRIPTION OF THE PREFERRED EMBODIMENT

This patent application is intended to describe one or more embodiments of the present invention. It is to be understood that the use of absolute terms, such as "must," "will," and the like, as well as specific quantities, is to be construed as being applicable to one or more of such embodiments, but not necessarily to all such embodiments. As such, embodiments of the invention may omit, or include a modification of, one or more features or functionalities described in the context of such absolute terms.

Figure 1:
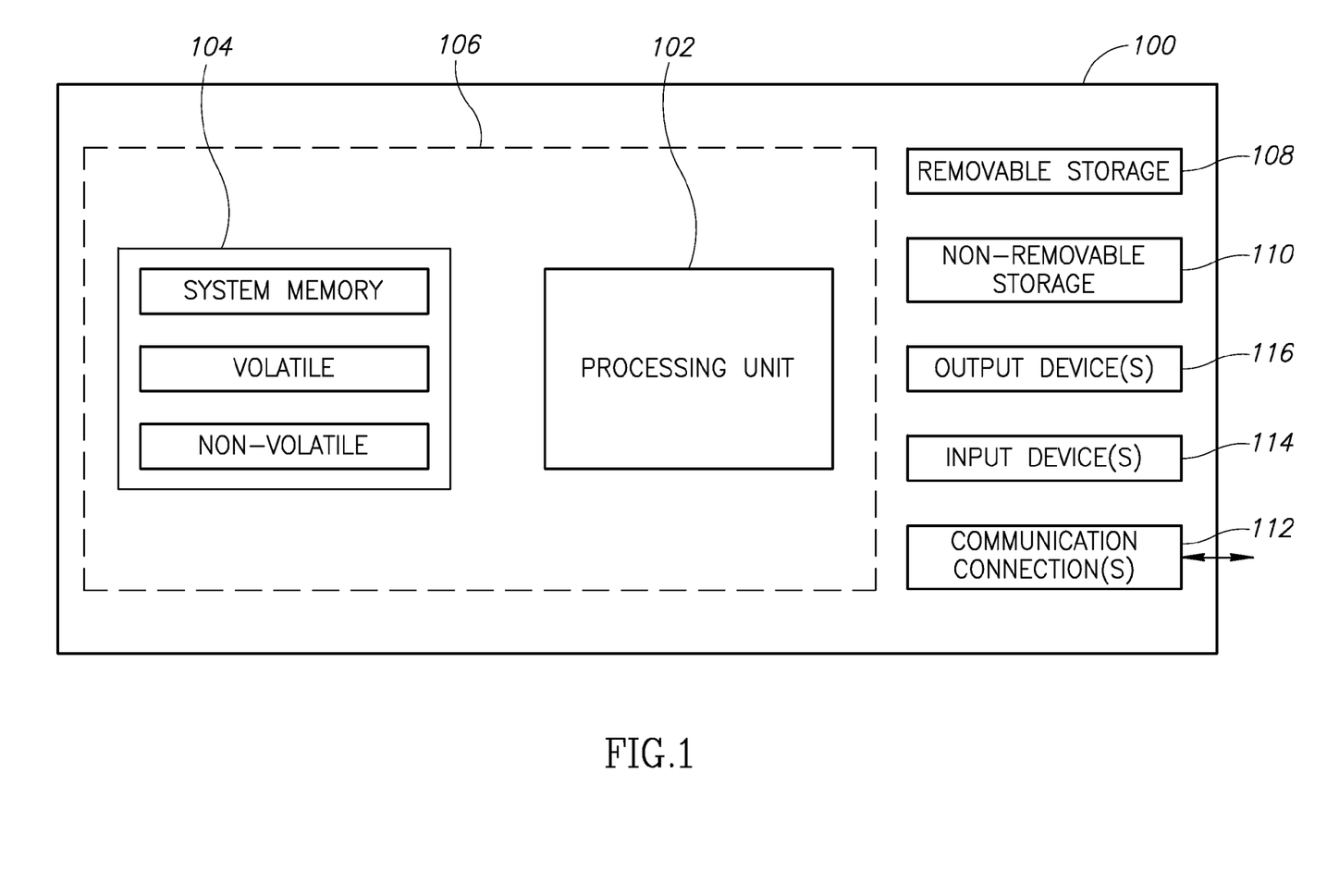
FIG. 1 illustrates an example of a computing system environment 100 in which an embodiment of the invention may be implemented.

FIG. 1 illustrates an example of a computing system environment 100 in which an embodiment of the invention may be implemented. The computing system environment 100, as illustrated, is an example of a suitable computing environment; however it is appreciated that other environments, systems, and devices may be used to implement various embodiments of the invention as described in more detail below.

Embodiments of the invention are operational with numerous general-purpose or special purpose computing system environments or configurations. Examples of well-known computing systems, environments, and/or configurations that may be suitable for use with embodiments of the invention include, but are not limited to, personal computers, server computers, hand-held or laptop devices, multi-processor systems, microprocessor-based systems, set-top boxes, programmable consumer electronics, network PCs, minicomputers, mainframe computers, distributed computing environments that include any of the above systems or devices, and the like.

Embodiments of the invention may be described in the general context of computer-executable instructions, such as program modules being executed by a computer. Generally, program modules include routines, programs, objects, components, data structures, etc. that perform particular tasks or implement particular abstract data types. Embodiments of the invention may also be practiced in distributed-computing environments where tasks are performed by remote processing devices that are linked through a communications network. In a distributed computing environment, program modules may be located in both local and remote computer storage media including memory storage devices. Additionally, the entity that may implement, or otherwise provide the ability to implement, elements of embodiments of the invention may be referred to herein as an "administrator."

With reference to FIG. 1, an exemplary system for implementing an embodiment of the invention includes a computing device, such as computing device 100. The computing device 100 typically includes at least one processing unit 102 and memory 104.

Depending on the exact configuration and type of computing device, memory 104 may be volatile (such as random-access memory (RAM)), nonvolatile (such as read-only memory (ROM), flash memory, etc.) or some combination of the two. This most basic configuration is illustrated in FIG. 1 by dashed line 106.

Additionally, the device 100 may have additional features, aspects, and functionality. For example, the device 100 may include additional storage (removable and/or non-removable) which may take the form of, but is not limited to, magnetic or optical disks or tapes. Such additional storage is illustrated in FIG. 1 by removable storage 108 and non-removable storage 110. Computer storage media includes volatile and nonvolatile, removable and non-removable media implemented in any method or technology for storage of information such as computer-readable instructions, data structures, program modules or other data. Memory 104, removable storage 108 and non-removable storage 110 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by device 100. Any such computer storage media may be part of device 100.

The device 100 may also include a communications connection 112 that allows the device to communicate with other devices. The communications connection 112 is an example of communication media. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, the communication media includes wired media such as a wired network or direct-wired connection, and wireless media such as acoustic, radio-frequency (RF), infrared and other wireless media. The term computer-readable media as used herein includes both storage media and communication media.

The device 100 may also have an input device 114 such as keyboard, mouse, pen, voice-input device, touch-input device, etc. Further, an output device 116 such as a display, speakers, printer, etc. may also be included. Additional input devices 114 and output devices 116 may be included depending on a desired functionality of the device 100.

According to one or more embodiments, the combination of software or computer-executable instructions with a computer-readable medium results in the creation of a machine or apparatus. Similarly, the execution of software or computer-executable instructions by a processing device results in the creation of a machine or apparatus, which may be distinguishable from the processing device, itself, according to an embodiment.

Correspondingly, it is to be understood that a computer-readable medium is transformed by storing software or computer-executable instructions thereon. Likewise, a processing device is transformed in the course of executing software or computer-executable instructions. Additionally, it is to be understood that a first set of data input to a processing device during, or otherwise in association with, the execution of software or computer-executable instructions by the processing device is transformed into a second set of data as a consequence of such execution. This second data set may subsequently be stored, displayed, or otherwise communicated. Such transformation, alluded to in each of the above examples, may be a consequence of, or otherwise involve, the physical alteration of portions of a computer-readable medium. Such transformation, alluded to in each of the above examples, may also be a consequence of, or otherwise involve, the physical alteration of, for example, the states of registers and/or counters associated with a processing device during execution of software or computer-executable instructions by the processing device.

As used herein, a process that is performed "automatically" may mean that the process is performed as a result of machine-executed instructions and does not, other than the establishment of user preferences, require manual effort.

Figure 2:
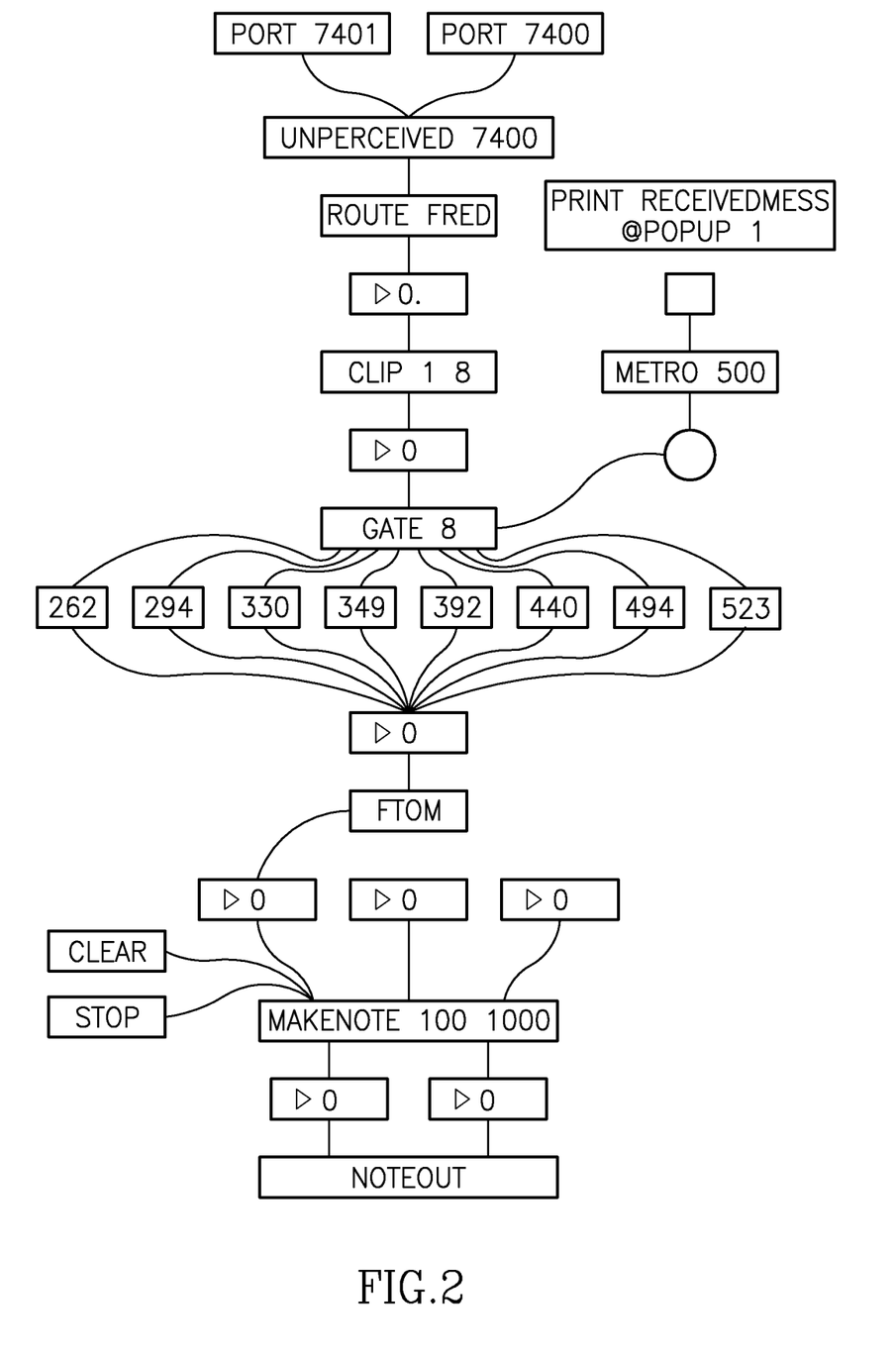
FIG. 2 illustrates a functional block diagram illustrating features of at least one embodiment of the invention.

FIG. 2 is a functional block diagram illustrating features of at least one embodiment of the invention.

An embodiment provides a system and method to generate music and sound controlled by a user via electroencephalogram (EEG) brain waves.

Prior approaches in this general area of endeavor incorporate the use of EEG waveform analysis or gaze control as measured by EEG. However, these approaches are not directly used for affirmative, as opposed to passive, control of sound and music.

An embodiment of the invention includes four basic elements: 1) Electroencephalogram (EEG) electrical brain activity signal, from scalp electrodes placed on the user, is measured in real time or near real-time by means of an amplifier, and converted from analog to digital signal. 2) This signal is sent to a computer, such as device 100, which, by executing computer-readable instructions according to an embodiment of the invention, processes the signal by multiple filters. This enables extracting the relative power of relevant waveforms (e.g. posterior dominant alpha rhythm or mu rhythm), resulting in a continuous sampling of this relative power (refer to Signal Processing Matlab Code as well as Timer Callback Matlab Code for original source code in Matlab program). 3) The device performs a training session, during which relative power of relevant waveforms are recorded for different cued conditions (e.g. posterior dominant alpha or motor mu rhythm) 'on' and 'off', and the device is thus automatically calibrated for each individual for each session. 4) After the training session calibration, the device enters into a free-running mode where the resulting numerical data is processed to convert this number/numbers into music (e.g. musical notes, chords, rhythms) or sound (refer to Music Synthesizer Max/MSP Code for original source-code in Max/MSP program) for use as a musical instrument or for neurological rehabilitation therapy.

Thus the user is able, in real time, to volitionally control music or sound by means of intentionally changing conscious cognitive processes, without any movement or vocalization on the part of the user, as measured by EEG brain waves.

An embodiment provides the use of EEG to generate music or sound in a manner that is demonstrably controllable by the user/subject without movement or vocalization on the part of the user. An embodiment provides the use of a cued training session prior to each individual use in order to calibrate the instrument. The device could be used to control the generation of musical notes, musical passages, unique sounds, or the playback of previously recorded music or sound.

Consequently, one or more embodiments of the invention provide the following features and/or uses:

A novel musical instrument for live performance

A novel music or sound generator for art installations

A novel therapeutic medical device for neurologically disabled patients

A novel diagnostic medical device for monitoring of neurological patients

1. Signal Processing Matlab Code—Processes EEG Signal

```
channel list={'Fp1','Fp2'};
fs=500;
f1=8;f2=12;
Wn=[f1 f2]*2/fs;
% channel 3 i.e. [18]-1 is actually O1
clist=[9 11 18 19]-1; % channels to use
[b,a]=butter(4,Wn);
global audio_on;
global audio_off;
[y,Fs]=audioread('on.wav');
audio_on=audioplayer(y, Fs);
[y,Fs]=audioread('off.wav');
audio_off=audioplayer(y, Fs);
global ntrial; % number of eyes open/eyes closed trials
ntrial=10;
global stim_period;
stim_period=20; % duration of eyes open/eyes closed
global trial_data; % holds the trial data for the stim period
global trial_timer; % counts the callback number within each trial
trial_timer=1;
trial_data=zeros(stim_period,length(clist),ntrial*2);
global current_trial;
current_trial=1; % counts the number of trials
global stim_state; % eyes open or closed;
stim_state=[1 2];
global data_buffer;
global data_buffer_cnt;
data_buffer=zeros(250000,numel(clist));
data_buffer_cnt=1;
global my_filter; % butterworth filter
global my_ma; % need a moving average to compute instantaneous power
global my_plot;
% all buffer values are in units of callback rate, i.e. my_fraction=10
% means buffer_size of 5000 is 500 s.
% same for training start etc.
global buffer_counter; % counts entries into a buffer
global buffer; % this holds the real time measured alpha values
buffer_size=5000; % holds 5000 power measurements
global training_period; % use this many samples to set up the histogram
global training_start; % start training after this many samples
global timer_counter; % this counts the timer callbacks
timer_counter=0;
training_start=20; % start collecting training data after 100/my_fraction (see below) s
training_period=ntrial*2*stim_period; % keep collecting training data for 2000/my_fraction (see below) s
global training_buffer; % holds the training data
training_buffer=zeros(training_period,numel(clist));
if (training_start+training_period>buffer_size)
buffer_size=training_start+training_period;
end
global octiles; % holds the thresholds for each channel
octiles=zeros(7,numel(clist));
buffer=zeros(buffer_size,numel(clist));
buffer_counter=1;
my_plot.f=figure;
my_plot.buffer=zeros(100,numel(clist));
my_plot.buffer_counter=1;
my_plot.channel=3; % this is the channel in the channel list that we plot
my_plot.p=plot(buffer(:,my_plot.channel));
% define a global UDP socket here
my_fraction=2; % defines the time period over which the power is averaged=1/(my_fraction) seconds
rate=1/my_fraction;
global ns0
ns0=round(fs/my_fraction); % get this many data points from the amps each [rate] sec
my_ma.b=ones(2*round(fs/my_fraction),1);
my_ma.b=my_ma.b/length(my_ma.b);
my_ma.res=[ ];
my_filter.res=[ ];
my_filter.a=a;
my_filter.b=b;
% for i=1:numel(clist)
%   Data=double(EEGStudio_Client.Methods.GetNewData(clist(i))); % get d
% end
my_timer=timer('TimerFcn',{@my_timer_callback, clist}, 'Period', rate,'ExecutionMode', 'fixedRate'); % specify channel number here
start(my_timer); % starts the timer
```

2. Timer Callback Matlab Code—Obtains Electrode Data, Sends Data to UDP Socket

```
function my_timer_callback(obj,event,channel)
global current_trial;
global trial_data; % holds the trial data for the stim period
global trial_timer; % counts the callback number within each trial
global ntrial; % number of eyes open/eyes closed trials
global audio_on; % contains the audio data to play for stimulation
global audio_off;
global my_filter;
global my_ma;
global my_plot;
global buffer_counter; % counts entries into a buffer
global buffer; % this holds the real time measured alpha values
global training_period; % use this many samples to set up the histogram
```

```
global training_start; % start training after this many
    samples
global timer_counter; % this counts the timer callbacks
global training_buffer; % holds the training data
global octiles;
global data_buffer;
global data_buffer_cnt;
global stim_period;
global stim_state;
stimulus_type={'eyes open','eyes closed'};
state=0;
if timer_counter>training_start && timer_counter<=
    (training_start+training_period)
    state=1;
end
% once finished with training do this only once
if timer_counter==(training_start+training_period+1)
    training_buffer=sort(training_buffer); % sorts data in
        buffer in ascending order
    for q=1:7
        octiles(q,:)=training_buffer(round(training_period/
            8*q),:); % generates borders of octiles
    end
end
if timer_counter>training_start+training_period
    state=2;
end
% the system can be in one of 3 states
% 0—the initialization period—nothing happens here
% 1—training period, this builds the histogram of alpha
    power for each
% channel
% 2—feedback period—send normalized data to sound
    program
state_out={'init','train','BCI' };
mp=zeros(numel(channel),1); % mean power for each
    channel, initialized here
val=mp; % val contains the position in the octile for each
    channel, yet to be calculated, see below
global ns0;
Data=zeros(ns0,numel(channel));
nav=EEGStudio_Client.Methods.GetTicksCount( ); %
    gets the current sample position from the EEG
for i=1:numel(channel) % go through each channel in
    'channel'
    inp=double(EEGStudio_Client.Methods.GetRange
        (channel(i),nav-ns0,ns0))'; % pull ns0 samples for
        that channel
    Data(:,i)=inp; % put these samples into a time x chan-
        nel array Data
end
% Data(:,1)=Data(:,3)-Data(:,1);
[dataf,my_filter.res]=filter(my_filter.b,my_filter.a,Data,
    my_filter.res); % filter it
[powerf,my_ma.res]=filter(my_ma.b,1,dataf.^2,my-
    _ma.res); % average power
data_buffer(data_buffer_cnt:data_buffer_cnt+ns0-1,:)
    =Data; % put the raw data into data_buffer
data_buffer_cnt=data_buffer_cnt+ns0; % move the
    data_buffer pointer up by ns0
mp=mean(powerf); % compute average power over the
    whole time period
% do any computation on the channel data
buffer(buffer_counter,:)=mp; % buffer the mean power
if state==1% if in training state, just record the mean
    power for each callback
    training_buffer(timer_counter-training_start,:)=mp;
trial_data(trial_timer,:,current_trial)=mp;
if current_trial==1 && trial_timer==1
    fprintf('starting training session\n');
    play(audio_on)
end
trial_timer=trial_timer+1;
if trial_timer>stim_period||current_trial==0% initiate
    new trial
    fprintf('changing from % s to % s % i trials of %
        i\n',stimulus_type {stim_state(1)},stimulus_type
        {stim_state(2)},current_trial,ntrial*2)
    h=stim_state(1);
    stim_state(1)=stim_state(2);
    stim_state(2)=h;
    switch h
        case 1
            play(audio_off)
        case 2
            play(audio_on)
        otherwise
    end
    current_trial=current_trial+1;
    trial_timer=1;
end
a=osc_new_address('10.107.107.108', 7400);
s=osc_new_server(7400); % change the port number if
    it throws an error involving the server
val_out=0; % this only sends out channel #3 in the list
m=struct('path', 'fred', 'data', {{single(val_out)}});
osc_send(a, m);
m=struct('path', 'counter', 'data', {{single(timer-
    _counter)}});
osc_send(a, m);
osc_free_server(s);
osc_free_address(a);
end
if state==2% if in BCI state, look up the octile position for
    mean power and put it into val, one position per
    channel
    val=sum(octiles<repmat(mp,7,1))+1;
end
% fprintf('% i % i % i\n',data_buffer_cnt')
if state==2% only send values after training
    % osc sender here:
    % a=osc_new_address('192.168.15.109', 7400);
    a=osc_new_address('10.107.107.108', 7400);
    s=osc_new_server(7400); % change the port number if
        it throws an error involving the server
    % for j=1:length(val)
    % val_out=val(j); % this only sends out channel #3 in
        the list
    % m=struct('path', 'fred', 'data', {{single(val_out)}});
    % osc_send(a, m);
    % end
    val_out=val(3); % this only sends out channel #3 in the
        list
    m=struct('path', 'fred', 'data', {{single(val_out)}});
    osc_send(a, m);
    m=struct('path', 'counter', 'data', {{single(timer_
        counter)}});
    osc_send(a, m);
    osc_free_server(s);
```

```
    osc_free_address(a);
    % osc sender above
end
% write e.g. mean(powerf) to the global UDP socket here
fprintf('% s',state_out {state+1});fprintf('% i',val);fprintf
    ('\n');
buffer_counter=buffer_counter+1;
if buffer_counter>numel(buffer)
    buffer_counter=1;
    fprintf('cycling buffer\n');
end
timer_counter=timer_counter+1; % increase the timer-
    _counter with every callback
set(my_plot.p,'YData',buffer(:,my_plot.channel));draw-
    now;
% set(my_plot.p,'YData',dataf);ylim([-200 200]);draw-
    now;
```

3. Music Synthesizer Max/MSP Code:

An embodiment of the invention includes three basic elements: 1) Electroencephalogram (EEG) electrical brain activity signal, from scalp electrodes placed on the user, is measured in real time or near real-time by means of an amplifier, and converted from analog to digital signal. 2) This signal is sent to a computer, such as device 100, which, by executing computer-readable instructions according to an embodiment of the invention, processes the signal by multiple filters. This enables extracting the relative power of relevant waveforms (e.g. posterior dominant rhythm or mu rhythm), resulting in a continuous sampling of this relative power (refer to Signal Processing Matlab Code as well as Timer Callback Matlab Code for original source-code in Matlab program). 3) The resulting numerical data is processed to convert this number/numbers into music (e.g. musical notes, chords, rhythms) or sound (refer to Music Synthesizer Max/MSP Code for original source-code in Max/MSP program).

Thus the user is able, in real time, to volitionally control music or sound by means of intentionally changing conscious cognitive processes, without any movement or vocalization on the part of the user, as measured by EEG brain waves.

An embodiment provides the use of EEG to generate music or sound in a manner that is demonstrably controllable by the user/subject without movement or vocalization on the part of the user. This could be used to control the generation of musical notes, musical passages, unique sounds, or the playback of previously recorded music or sound.

Consequently, one or more embodiments of the invention provide the following features and/or uses:

A novel musical instrument for live performance
A novel music or sound generator for art installations
A novel therapeutic medical device for paralyzed patients
A novel diagnostic medical device for monitoring of neurological patients 1. Signal Processing Matlab Code—Processes EEG Signal

```
    fs=500;
    f1=8;f2=12;
    Wn=[f1 f2]*2/fs;
    [b,a]=butter(4,Wn);
    global my_filter; % butterworth filter
    global my_ma; % need a moving average to compute
instantaneous power
    global my_plot;
    my_plot.f=figure;
    my_plot.buffer=zeros(100,1);
    my_plot.buffer_counter=1;
    my_plot.p=plot(my_plot.buffer);
    % define a global UDP socket here
    my_fraction=10; % defines the time period over which the
power is averaged=1/(my_fraction) seconds
    my_ma.b=ones(round(fs/my_fraction),1);
    my_ma.b=my_ma.b/length(my_ma.b);
    my_ma.res=[ ];
    my_filter.res=[ ];
    my_filter.a=a;
    my_filter.b=b;
    my_timer=timer('TimerFcn',{@my_timer_callback,1},
'Period', .1,'ExecutionMode', 'fixedRate'); % specify channel number here
    start(my_timer); % starts the timer
```

2. Timer Callback Matlab Code—Obtains Electrode Data, Sends Data to UDP Socket

```
    function my_timer_callback(obj,event,channel)
    global my_filter;
    global my_ma;
    global my_plot;
    Data=double(EEGStudio_Client.Methods.GetNewData
(channel)); % get data from channel
    [dataf,my_filter.res]=filter(my_filter.b,my_filter.a, Data',
my_filter.res); % filter it
    [powerf,my_ma.res]=filter(my_ma.b,1,dataf.^2,my_
ma.res); % average power
    % osc sender here:
    a=osc_new_address('192.168.15.109', 7400);
    s=osc_new_server(3333); % change the port number if it
throws an error involving the server
    m=struct('path','fred','data',           {{single(mean
(powerf,1))}});
    osc_send(a, m);
    osc_free_server(s);
    % osc sender above
    % write e.g. mean(powerf) to the global UDP socket here
    fprintf('% f\n',mean(powerf,1))
```

A novel musical instrument was created using electroencephalogram (EEG) motor imagery to control a synthesized piano, and is herein named the Encephalophone. Alpha-frequency (8-12 Hz) signal power, originating from either posterior dominant rhythm (PDR) in the occipital cortex or from mu rhythm in the motor cortex, was used to create a power scale which was then converted into a musical scale which could be manipulated by the individual. Subjects could then generate different notes of the scale by activation (event-related synchronization) or de-activation (event-related desynchronization) of the PDR or mu rhythms in occipital or motor cortex, respectively. 13 normal subjects were tested in their ability to hit target notes presented within a five-minute trial period. All 13 subjects were able to perform more accurately (average of 26.2 hits, 67.1% accuracy) than a random note generator (8.4 hits, 26.6% accuracy) when using visual cortex/PDR signaling; all 13 subjects were also more accurate (average of 19.0 hits, 53.7% accuracy) than a random note generator using motor imagery/mu signaling. This paper describes the creation of the Encephalophone, and describes studies proving the accuracy of the instrument in generating musical notes using motor imagery without muscle movement. The Encephalophone's accuracy will be improved by training within the musical context, and has future applications as a novel musical instrument without requiring movement, as well as a potential therapeutic device for patients suffering from motor deficits (e.g. Amyotrophic lateral sclerosis, brainstem stroke, traumatic amputation).

A Mitsar 201 EEG (Mitsar Co., Ltd., St. Petersburg, Russia; distributed by Nova Tech, Inc., Mesa, Ariz.) and 19-channel ElectroCap electrode cap (Electro-Cap International Inc., USA) were used to collect EEG signal utilizing the International 10-20 system of electrode placement from 13 normal human volunteer subjects.

Subjects were recruited by asking students in a graduate music program and by asking personal contacts for volunteers. Written informed consent was obtained from each subject prior to testing, and subjects had the opportunity to withdraw from the study at any time. Given experiments were conducted using commercially available equipment in a private music studio with negligible risk to participants, institutional review board (IRB) approval was not deemed necessary. As no IRB existed for this music studio, an IRB was not approached for a waiver of permission.

Subjects were positioned in a relaxed, reclining position with a headrest to minimize muscle artifact, and were positioned facing away from computer screens and other equipment to eliminate visual feedback. The primary EEG signal at a sampling rate of 500 Hz was initially processed in a HP Pavilion PC (Hewlett-Packard, Palo Alto, Calif.) with Mitsar EEG Acquisition software, where filters were applied (100 Hz low-pass, 0.5 Hz high-pass, and 60 Hz notch filters). Primary EEG signal was visually verified by a physician clinical neurophysiologist for good signal quality and lack of artifact. EEG data was then streamed in real time to Matlab (The MathWorks, Inc., Natick, Mass.) via the Mitsar Matlab API.

Matlab scripts for real-time signal processing were created to apply Butterworth filters and generate alpha frequency (8-12 Hz) power for the posterior dominant rhythm (visual cortex) signal power from occipital electrodes (O1) or motor cortex mu rhythm signal power from motor cortex electrodes (C3 for right hand motor imagery) in real time. Real time power estimates were computed by applying a fourth order butterworth bandpass filter to incoming segments of 500 ms of data. The bandpass filtered data was rectified and then averaged over the entire segment length to produce a single power estimate for every 500 ms segment. For motor imagery, subjects were instructed to imagine right hand grasping and opening at a rate of approximately 1 Hz as per prior motor imagery BCI methods of Neuper et al. [9].

A training period was created for each individual subject and each individual trial session of the Encephalophone. The training period consisted of alternating cued states ("on" or "off"). For visual cortex posterior dominant rhythm, an auditory cue of "on" cued the eyes closed, awake state, and "off" cued the eyes open, awake state. For motor cortex mu rhythm, an auditory cue of "on" cued the awake, resting state, and "off" cued motor imagery of right hand movement state. This training period established the full range of values of alpha frequency power for an individual subject and individual trial session in the different cued states, then generated eight equal sized 'bins', or ranges of values, based on the training period alpha power histogram. Thus visual cortex posterior dominant rhythm and motor cortex mu alpha frequency power is converted to an absolute number from 1 to 8 for each individual, where each value (1-8) has an equal probability to occur under the training regime.

After the training period is used to calibrate the instrument to each individual, the device enters the free-running period, during which values from 1 to 8 are continuously generated in real-time from the desired alpha frequency power (posterior dominant rhythm or mu rhythm) of the user.

This free-running stream of values from 1 to 8 in Matlab is sent at a rate of one value per 500 msec (120 bpm musical tempo for quarter notes) using OSC (Open Sound Control) along an Ethernet cable via a router to a second computer—an Apple MacBook Pro (Apple, Inc. USA)—where it is received by Max/MSP music generation software (Cycling '74, USA). The signal is used to generate notes in the C major scale with a synthesized piano tone (8 notes from C4 to C5).

For note accuracy experiments, the subject is presented with a target note of either a high C (C5) or low C (C4). The subject generates one note every 500 msec and attempts to match the note or its nearest neighbor 3 times consecutively. If the note is successfully matched 3 times consecutively, a 'hit' is scored and a reward chord (C major) is played, then a new target note is presented. If the subject does not hit the target note 3 times consecutively within 9.5 seconds (19 notes), a 'miss' is scored and an error chord (tritone) is played, then a new target note is presented. This results in a chance probability of 26.56% to score a 'hit' over the interval. A total of 300 seconds, or 5 minutes, is given for each trial, and the results recorded.

13 normal volunteer subjects were trained and tested for musical accuracy using the Encephalophone using both posterior dominant rhythm (PDR) control and motor mu rhythm control (basic demographics shown in Table 1). Subjects underwent one 5 minute training period to calibrate the instrument, followed by a brief (3 minute) free-run practice period, then a 5 minute accuracy trial for each of PDR and mu control. Results from these musical accuracy experiments were recorded for individual number of hits, trials, percent accuracy, and chance probabilities for each 5 minute trial using PDR control and mu control (summary shown in Table 2).

TABLE 1

Subject Demographics

| Subject # | Age | Gender | Years Musical Training |
|---|---|---|---|
| 1 | 27 | M | 18 |
| 2 | 63 | M | 3 |
| 3 | 44 | M | 18 |
| 4 | 37 | M | 0 |
| 5 | 35 | M | 0 |
| 6 | 38 | F | 5 |
| 7 | 27 | M | 17 |
| 8 | 31 | M | 25 |
| 9 | 27 | M | 19 |
| 10 | 25 | F | 11 |
| 11 | 27 | F | 21 |
| 12 | 27 | M | 8 |
| 13 | 48 | M | 6 |
| Average | 35.1 | | 11.6 |

TABLE 2

Individual Subject Results from Accuracy Experiments.

| Subject # | PDR hits | PDR trials | PDR % | PDR Prob | Mu hits | Mu trials | Mu % | Mu Prob |
|---|---|---|---|---|---|---|---|---|
| 1 | 16 | 35 | 45.7 | 4.40E−03 | 17 | 35 | 48.6 | 1.50E−03 |
| 2 | 23 | 36 | 63.9 | 5.60E−07 | 32 | 41 | 78.0 | 8.80E−14 |
| 3 | 33 | 39 | 84.6 | 3.40E−15 | 25 | 39 | 64.1 | 1.90E−07 |
| 4 | 30 | 38 | 78.9 | 2.20E−12 | 16 | 33 | 48.5 | 2.00E−03 |
| 5 | 14 | 32 | 43.8 | 1.10E−02 | 17 | 33 | 51.5 | 6.00E−04 |
| 6 | 12 | 31 | 38.7 | 4.60E−12 | 27 | 40 | 67.5 | 1.20E−08 |

TABLE 2-continued

Individual Subject Results from Accuracy Experiments.

| Subject # | PDR hits | PDR trials | PDR % | PDR Prob | Mu hits | Mu trials | Mu % | Mu Prob |
|---|---|---|---|---|---|---|---|---|
| 7 | 14 | 32 | 43.8 | 1.10E−02 | 15 | 36 | 41.7 | 1.60E−02 |
| 8 | 52 | 55 | 94.5 | 0 | 19 | 34 | 55.9 | 7.40E−05 |
| 9 | 34 | 41 | 82.9 | 5.30E−15 | 19 | 33 | 57.5 | 4.00E−05 |
| 10 | 19 | 33 | 57.6 | 4.00E−05 | 15 | 33 | 45.5 | 5.70E−03 |
| 11 | 45 | 51 | 88.2 | 0 | 16 | 31 | 51.6 | 7.90E−04 |
| 12 | 24 | 27 | 88.9 | 7.90E−13 | 12 | 31 | 38.7 | 4.58E−02 |
| 13 | 25 | 41 | 61.0 | 8.30E−07 | 17 | 35 | 48.6 | 1.50E−03 |
| Average | 26.2 | 37.8 | 67.1 | 1.30E−08 | 19.0 | 34.9 | 53.7 | 1.30E−04 |
| Random | 8.4 | | 26.6 | | 8.4 | | 26.6 | |

PDR Prob and Mu Prob are the binomial cumulative distribution function for chance probability of scoring the given number of hits or higher in the given number of trials for each individual; a probability of zero indicates less than $1.0 \times 10^{-15}$ probability.

Figure 3A:
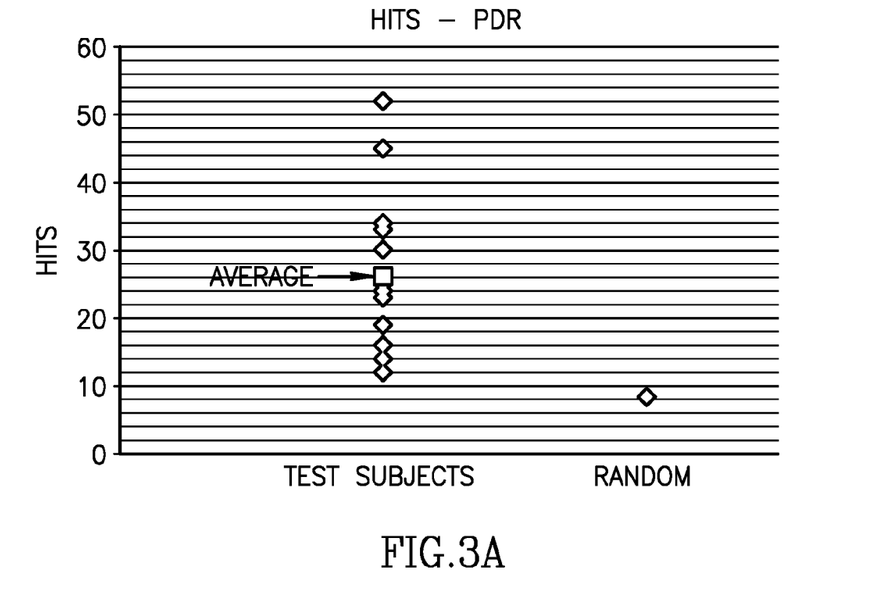
FIGS. 3A-3D illustrate Number of Notes Hit and Percent Accuracy for PDR and Mu Control.
Figure 3B:
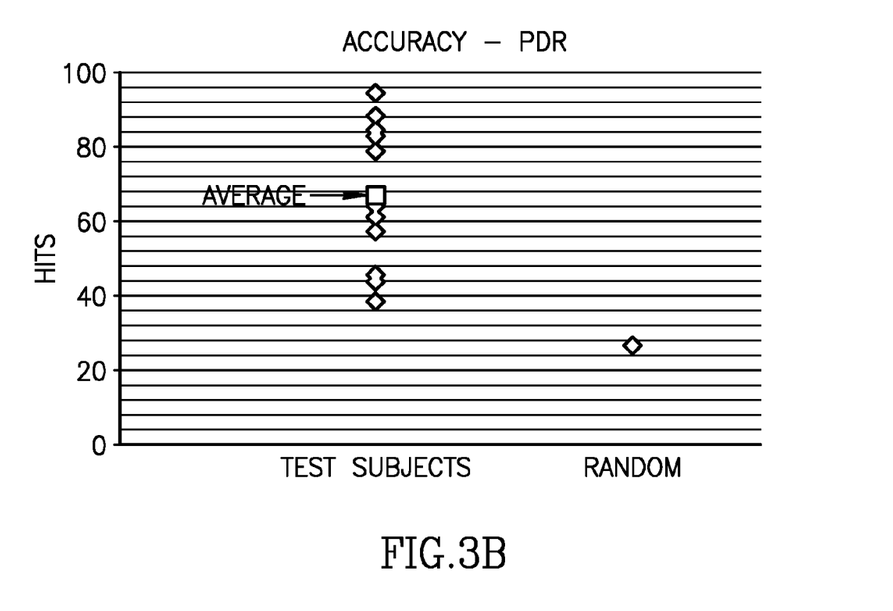
Figure 3C:
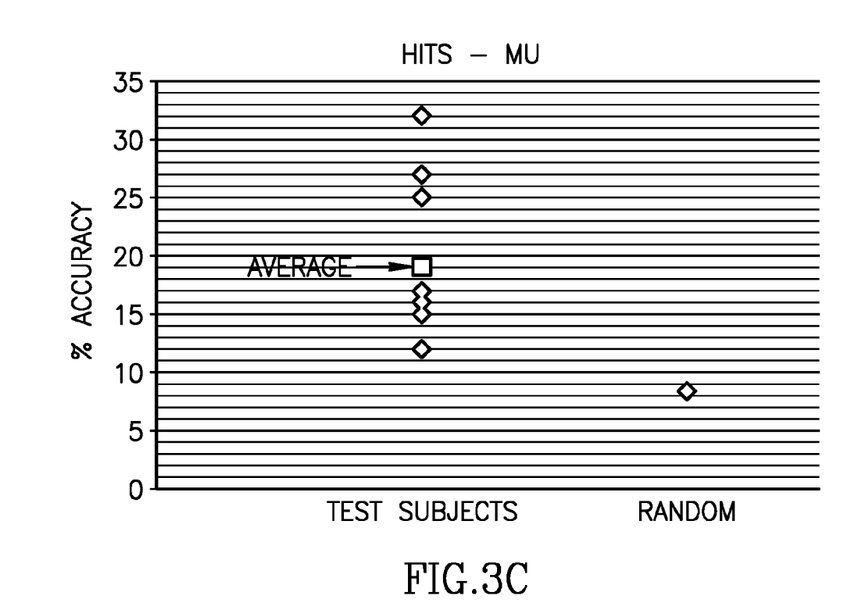
Figure 3D:
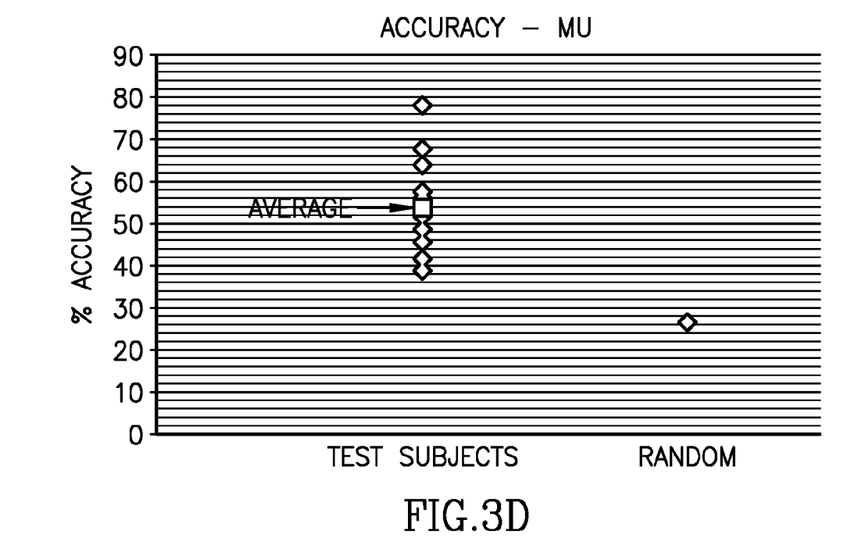
Figure 4A:
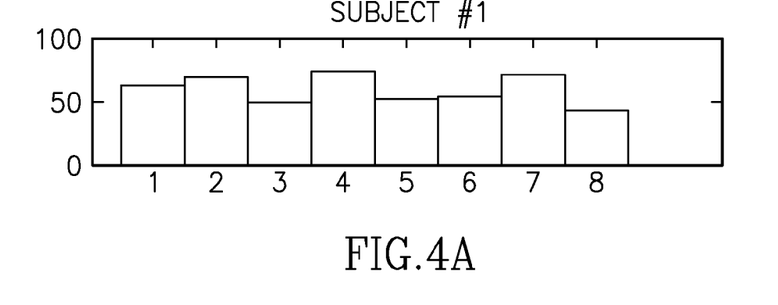
FIGS. 4A-4M and FIGS. 5A-5M illustrate Skew Bias for Individual Notes for Each Subject.
Figure 4B:
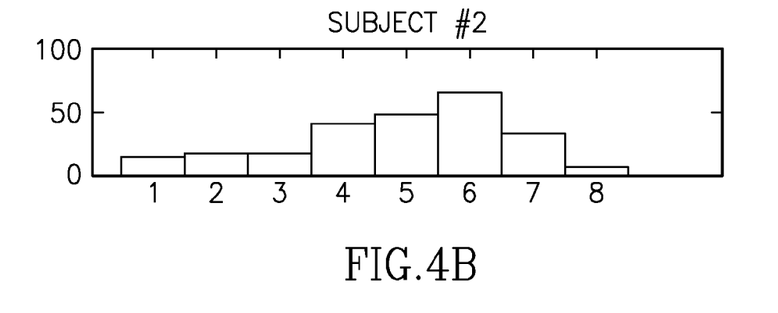
Figure 4C:
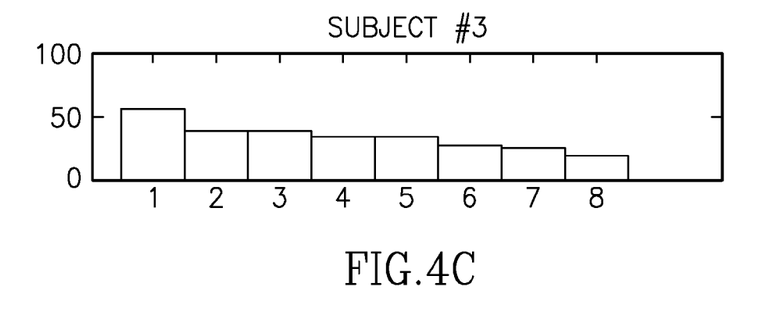
Figure 4D:
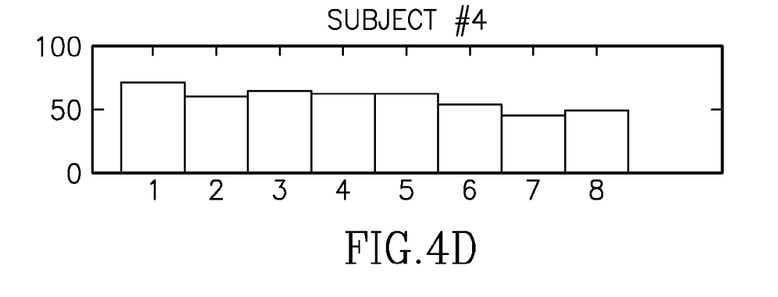
Figure 4E:
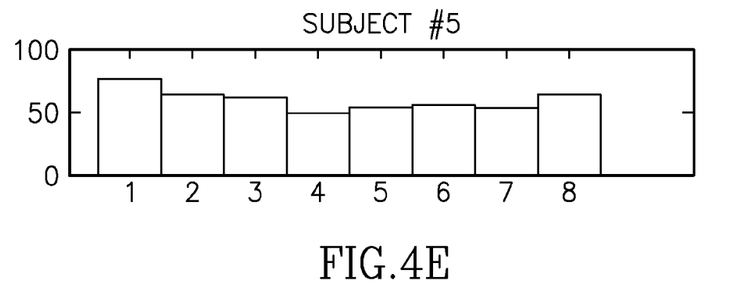
Figure 4F:
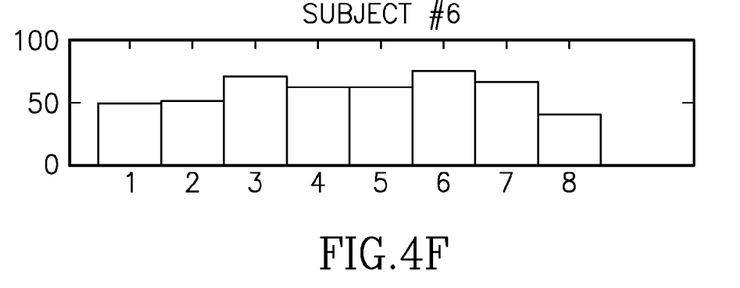
Figure 4G:
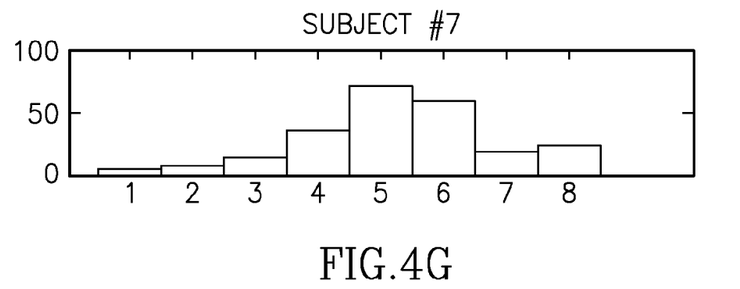
Figure 4H:
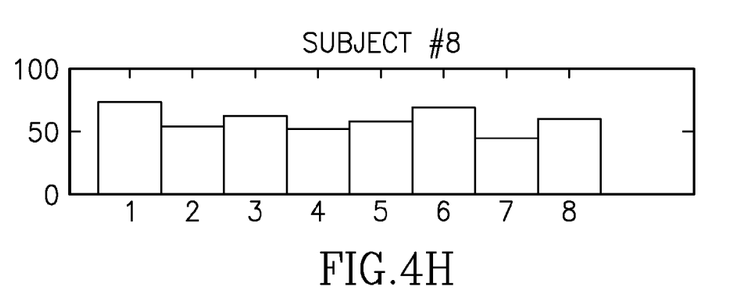
Figure 4I:
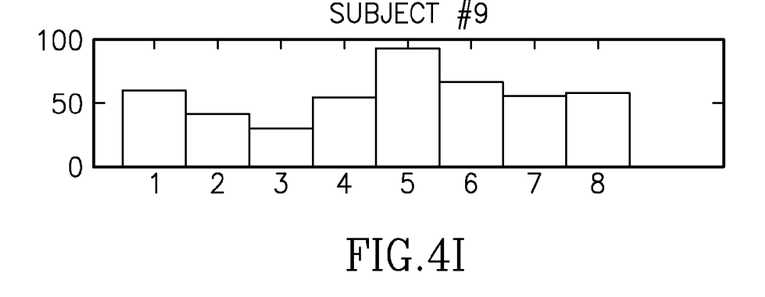
Figure 4J:
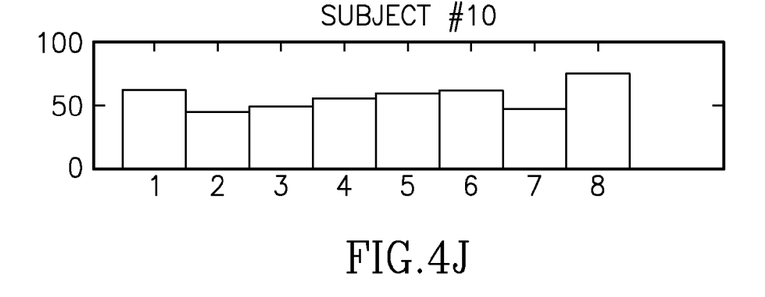
Figure 4K:
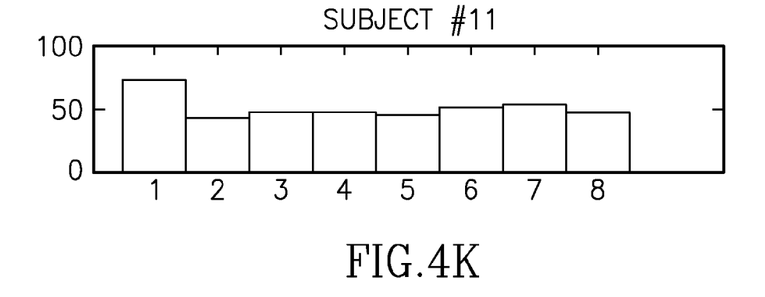
Figure 4L:
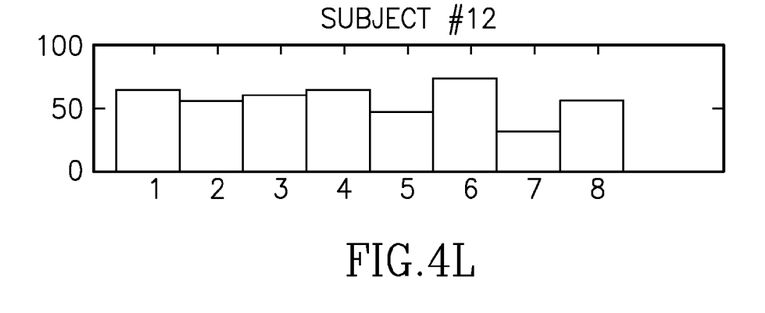
Figure 4M:
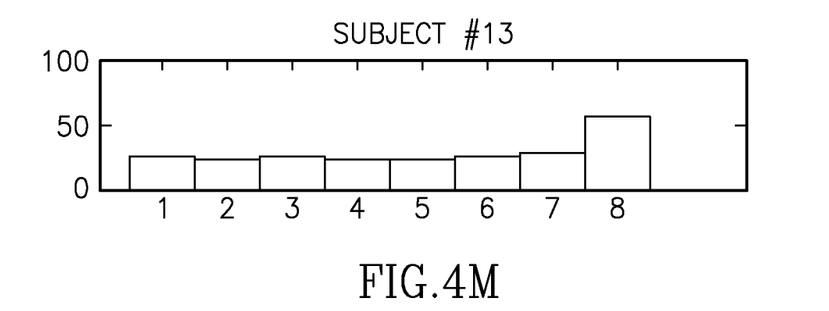
Figure 5A:
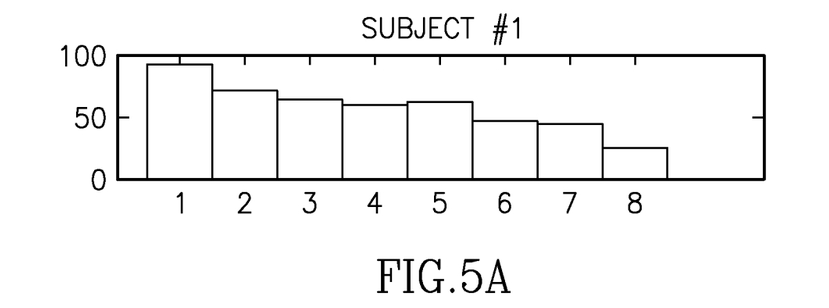
Figure 5B:
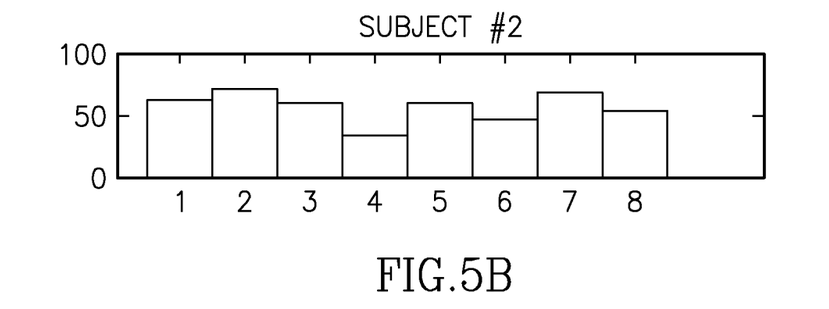
Figure 5C:
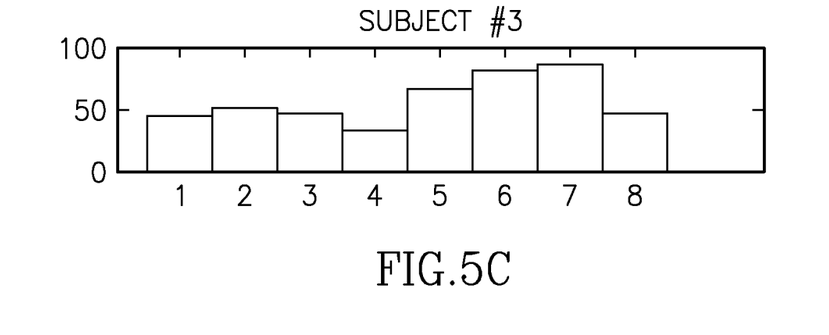
Figure 5D:
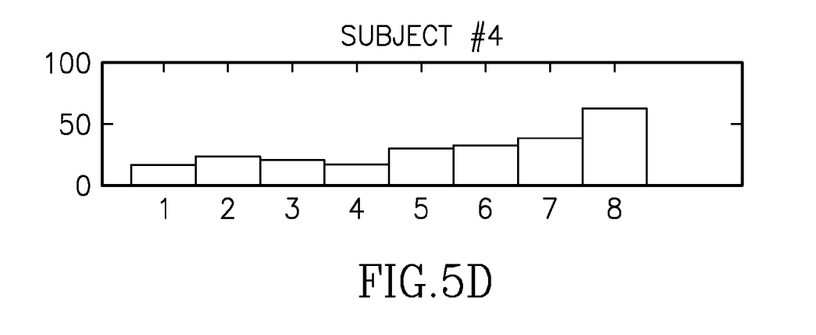
Figure 5E:
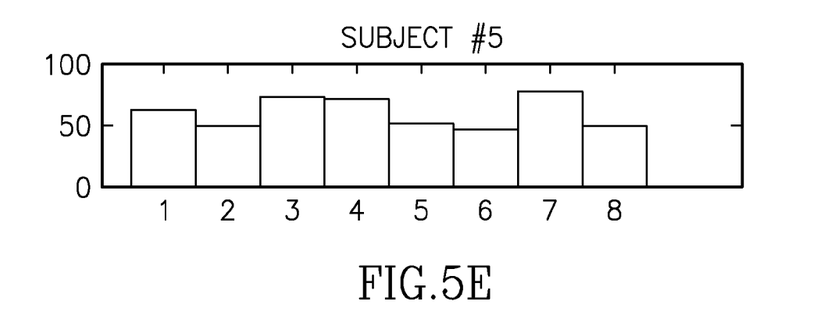
Figure 5F:
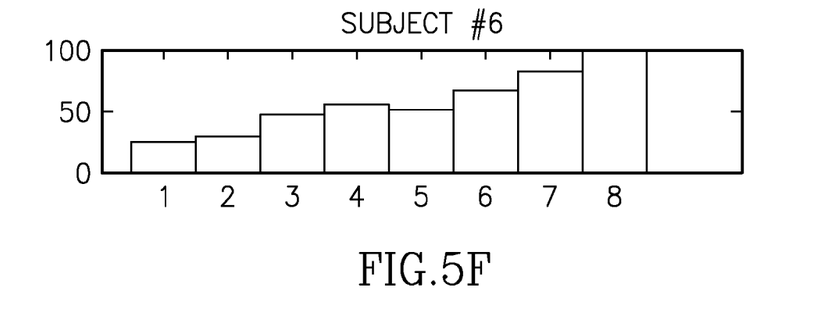
Figure 5G:
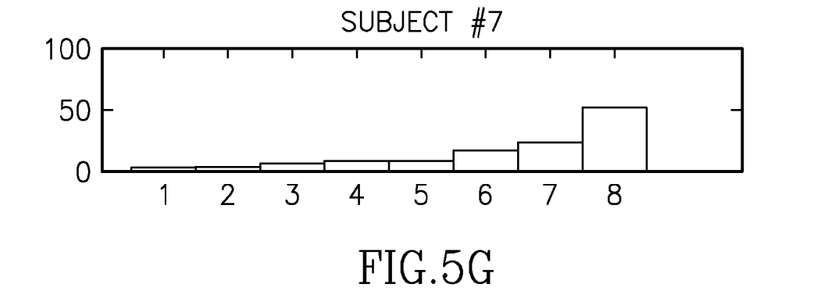
Figure 5H:
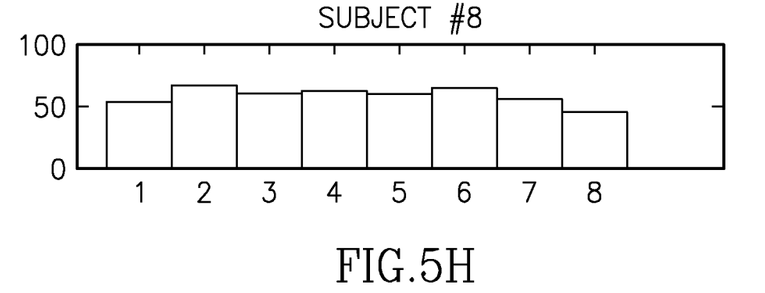
Figure 5I:
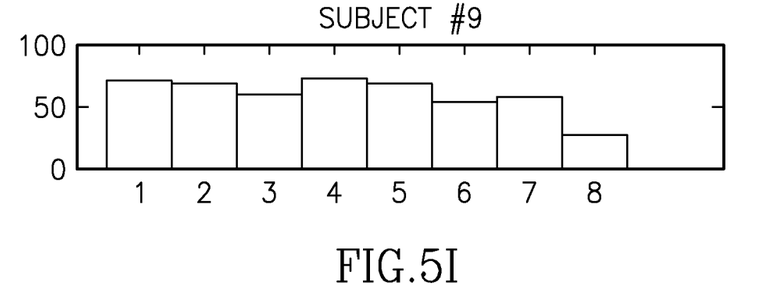
Figure 5J:
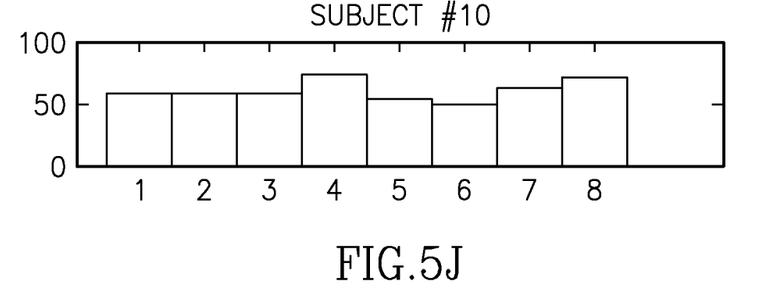
Figure 5K:
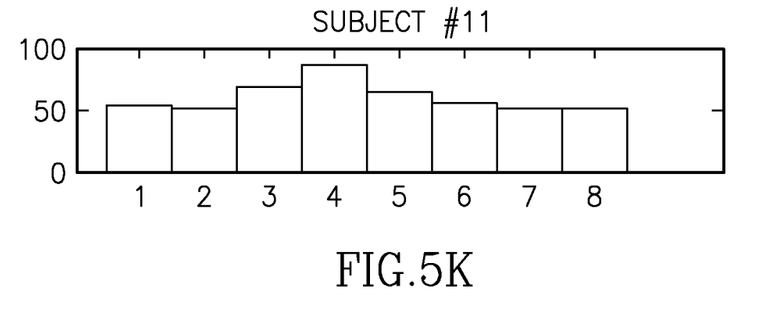
Figure 5L:
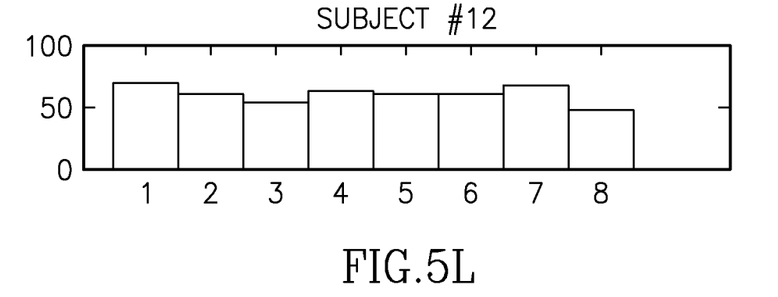
Figure 5M:
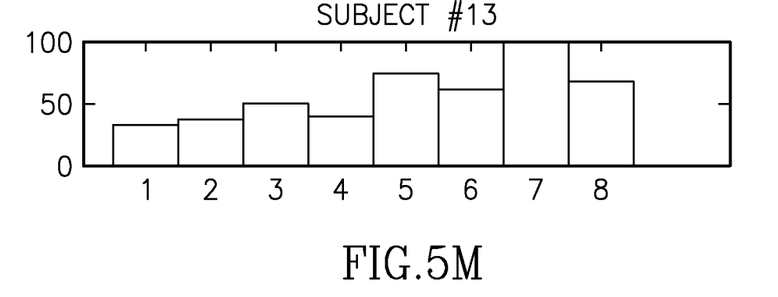

Subjects using PDR control had an average of 26.2 hits (FIG. 3a, $\sigma=12.2$) and 67.1% accuracy (FIG. 3b, $\sigma=20.1$), and using mu control had an average of 19.0 hits (FIG. 3c, $\sigma=5.6$) and 53.7% accuracy (FIG. 3d, $\sigma=10.9$). Random note generation within the C major scale generates an average of 8.4 hits and 26.2% accuracy. Each individual subject scored higher than random in both hits and accuracy for both PDR and mu control (FIG. 3). The chance probability of scoring a given number of hits or higher, calculated using the binomial cumulative distribution function, ranged from less than $1 \times 10^{-15}$ to $4.58 \times 10^{-2}$. There was a general trend towards increased PDR hits and accuracy—but not mu hits and accuracy—with increasing years of musical training, but this was not statistically significant.

FIGS. 3A-3D. Number of Notes Hit and Percent Accuracy for PDR and Mu Control. Individual subjects were given 5 minutes to hit as many target notes as possible using either PDR control or Mu control. Scatter plots of results of all subjects were generated, with average results and random control included, for each of: 3A. Number of hits using PDR control. 3B. Percent accuracy using PDR control. 3C. Number of hits using mu control. 3D. Percent accuracy using mu control.

In order to assess for individual subject bias skewed towards particular notes, histograms of note generation were created (FIG. 4). If an individual exclusively generated a high or low note, for example, this bias would result in scoring a hit in 50% of note trials. Extreme skew bias could occur, for example, if no alpha frequency signal was recorded during training, or if only noise and artifact were being measured. Most subjects did not show a large skew bias. The most significant skew bias occurred with mu control and subject #7. If we were to discard every high note target (to which this subject is heavily skewed), the subject would have scored 2 hits in 22 trials (9.1% accuracy). This likely represents significant bias in this most extreme case. However, the probability of scoring 15 or more hits by random note generation in 36 trials is only 1.6% (binomial cumulative distribution function).

FIG. 2. Skew Bias for Individual Notes for Each Subject. Histograms for each individual subject showing frequency of each of 8 possible notes for: 2a. PDR control experiment and 2b. Mu control experiment This paper describes the creation of the Encephalophone, a BCMI device and musical instrument, which uses motor imagery—without movement—to control notes of a musical scale in real time. We further test 13 normal subjects novice to the device in experiments to test accuracy in hitting a target note, and our results show each subject scoring higher than random, with the average score much higher than random. We additionally looked at skew bias for individual notes for each subject, and found most subjects without large skew bias. Even those subjects with larger biases were able to score hits at both ends of the note range. These studies demonstrate that the Encephalophone is effective at allowing cognitive volitional control of generation of musical notes with a fixed tempo, in real time.

We believe these results and the creation of this device is of significant interest for several reasons. First, we believe this is the first description of the creation of consciously controlled real-time EEG generation of scalar music by a user with experimentally proven accuracy. Second, given the strong emotional valence of music as both a stimulus and feedback modality, we believe this device has tremendous potential for greater accuracy than previous BCI devices with continued musical training. Subjects in this study underwent only 5 minutes of calibration and 3 minutes of free training before being tested experimentally. Given this already promising accuracy with novices, further intensive training that is musically motivated is likely to yield significantly higher accuracy and facility with the instrument. Third, the use of an auditory feedback-based BCI device with clear responsiveness to the user holds great promise for patients—such as those with locked in syndrome—who are severely incapacitated and may be far more likely to respond to auditory (specifically musical) stimulus and feedback than to visual stimulus and feedback.

The Encephalophone BCMI instrument described here is most effective at accurately generating notes at the highest and lowest parts of the scale (C5 and C4, respectively, here), although some control over passing tones is possible with partial or brief turning 'on' or 'off' of mu or PDR EEG rhythms. Thus the Encephalophone controls music using a range of consciously controlled values (in this case a C major scale), although is most effective in controlling the highest and lowest notes of the scale. The experiments described here primarily tested a binary control, as the target notes were limited to C5 and C4.

Previously, others have reported use of BCI to control not just visual output (e.g. cursor on computer screen) but sound, and reported better control and accuracy with visual rather than auditory feedback [10]. Here we report good control with virtually no training, using musical feedback rather than non-musical auditory feedback. We expect with further training and strongly motivational musical accompaniment, the rich musical context provided will greatly improve learning and accuracy of control. Music has strong, evolutionary based roots in human auditory and emotional communication, and would be expected to be a stronger stimulus and feedback than non-musical sound. The musical environment, particularly if well constructed with emotionally motivating accompaniment, should provide a much stronger paradigm to stimulate the learning of mapping cognitive processes to notes, chords, timbres, or voices. As with musical instruments requiring motor as well as cognitive learning such as the violin, we expect that given proper motivation, subjects using the Encephalophone will greatly improve in accuracy as the learning curve of the instrument is traversed.

BCI has had limited success for practical application in motor prostheses and computer cursor control, largely because reliable control of such devices requires a high degree of accuracy. However, for control of music (assuming algorithms in which occasional 'errors' are also heard as pleasing), the Encephalophone does not require the same degree of accuracy in order to make pleasing music that the user can feel an obvious influence over. Additionally, with the possibility of improved feedback and learning that the musical environment can motivate, if accuracy levels reach new heights with this device, such learning might then be used to improve non-musical control in the future.

This device is being used as a novel musical instrument in live performance, accompanied by small ensembles of musicians, as a novel improvisational instrument. Future development will include using multiple soloists performing with Encephalophones together, in a call and response improvisation, as well as performers improvising not only with musical scales, but also with timbre or chordal improvisation. Furthermore, work in computer music using conscious control of sound spatialization is being explored.

We also plan on using the Encephalophone in trials of cognitive rehabilitation and music therapy with patients with motor disabilities. Patients who might thus benefit would include patients suffering from amyotrophic lateral sclerosis (ALS), brainstem stroke, or traumatic amputation (such as war veterans). The ability to generate music using a portion of the brain that is no longer able to control motor movement of limbs is likely to be of significant emotional value to such patients, and might provide therapy for emotional disorders including PTSD. Additionally, the use of motor cortex that is disconnected from motor output to make music may improve cognitive rehabilitation, and cortical 'rewiring' of such circuits may allow new motor output pathways for regaining some motor control.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. An encephalophone, comprising:
   a plurality of electrodes configured to attach to a scalp of a user and transmit electrical brain activity signals received from the scalp; and
   a processing device configured to receive the signals from the electrodes, determine relative power levels of visual cortex posterior dominant rhythm (PDR) waveforms and motor cortex mu rhythm (mu) waveforms, correlate the relative power levels to multiple different cued conditions of the user, and convert the correlated power levels into at least one of musical notes and chords only within a specific predetermined scale.

2. The encephalophone of claim 1, wherein the electrodes are spaced according to the International 10-20 system of electrode placement.

3. An encephalophone, comprising:
   a plurality of electrodes configured to attach to a scalp of a user and transmit electrical brain activity signals received from the scalp; and
   a processing device configured to receive the signals from the electrodes, determine relative power levels of at least one of visual cortex posterior dominant rhythm (PDR) waveforms and motor cortex mu rhythm (mu) waveforms, correlate the relative power levels to multiple different cued conditions of the user, and convert the correlated power levels into at least one of musical notes and chords only within a specific predetermined scale.

4. An encephalophone, comprising:
   a plurality of electrodes configured to attach to a scalp of a user and transmit electrical brain activity signals received from the scalp; and
   a processing device configured to receive the signals from the electrodes, determine relative power levels of at least one of visual cortex posterior dominant rhythm (PDR) waveforms and motor cortex mu rhythm (mu) waveforms, correlate the relative power levels to multiple different cued conditions of the user, and convert the correlated power levels into musical notes only within a specific predetermined scale.

* * * * *